United States Patent [19]

Eibl et al.

[11] 4,160,773

[45] Jul. 10, 1979

[54] SYNTHETIC ALKYL ESTERS OF PHOSPHOLIPID ACID, STRUCTURAL ANALOGS THEREOF AND A PROCESS FOR THEIR MANUFACTURE AND THEIR USE

[75] Inventors: Hansjörg Eibl, Bovenden; Walter Diembeck, Göttingen; Stephan Kovatchev, Göttingen-Roringen, all of Fed. Rep. of Germany

[73] Assignee: Max-Planck-Gesellschaft zur Förderung der Wissenschaften e.V., Gottingen, Fed. Rep. of Germany

[21] Appl. No.: 868,735

[22] Filed: Jan. 12, 1978

Related U.S. Application Data

[63] Continuation of Ser. No. 602,030, Aug. 5, 1976, abandoned.

[30] Foreign Application Priority Data

Aug. 6, 1974 [DE] Fed. Rep. of Germany ....... 2437833

[51] Int. Cl.$^2$ .................... A23J 7/00; C07F 9/02; C11C 3/00
[52] U.S. Cl. .................... 260/403; 260/952; 260/973; 260/346.11; 252/356
[58] Field of Search ................ 260/952, 403

[56] References Cited

U.S. PATENT DOCUMENTS

| 3,577,446 | 5/1971 | Rakhit | 260/403 |
| 3,705,213 | 12/1972 | Pfeiffer | 260/403 |

*Primary Examiner*—John Niebling
*Attorney, Agent, or Firm*—Curtis, Morris & Safford

[57] ABSTRACT

Synthetic alkylesters of phospholipid acid, the structural analogues thereof, their physiologically acceptable salts as well as a process for preparing them and their use.

3 Claims, No Drawings

SYNTHETIC ALKYL ESTERS OF PHOSPHOLIPID ACID, STRUCTURAL ANALOGS THEREOF AND A PROCESS FOR THEIR MANUFACTURE AND THEIR USE

This is a continuation of application Ser. No. 602,030 filed Aug. 5, 1976, now abandoned.

The present invention relates to synthetic alkyl esters of phospholipid acid, the structural analogs and the physiologically acceptable salts thereof and to a process for their manufacture.

The process of the invention comprises (A) reacting a primary alcohol of the formula $$R_3OH \qquad \text{I}$$

wherein $R_3$ stands for a saturated or unsaturated straight-chain or branched alkyl group of one to 25 carbon atoms, which may be substituted by halogen, a cycloalkyl group or an aromatic group, with phosphorus oxychloride in the presence of an inert organic solvent, and (B) reacting the resulting phosphorylation agent of the formula

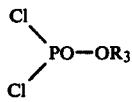

wherein $R_3$ is defined as above, with a polyhydroxy compound having a free hydroxy group and the further hydroxy groups of which are protected.

The process of the present invention permits the preparation of large numbers of alkyl esters of phospholipid acid by simply reacting a primary alcohol with phosphorus oxychloride. The resulting phosphorylation agent of formula II may be reacted directly without isolation with the polyhydroxy compound without having to distil the phosphorylation agent.

In the above formula I, $R_3$ may stand for a saturated or unsaturated straight-chain or branched alkyl group having 1 to 25 carbon atoms, for example 1 to 23, 1 to 21, 1 to 18, 1 to 16, 3 to 25, 3 to 23, 3 to 21, 3 to 18, 3 to 16, 3 to 14, 3 to 12, 3 to 10, 4 to 25, 4 to 21, 4 to 18, 4 to 16, 4 to 12, 6 to 25, 6 to 18 or 6 to 14 carbon atoms.

The group represented by $R_3$ may contain one or more double bonds or triple bonds and may be substituted by halogen, such as bromine, chlorine, iodine or fluorine. It may also be substituted by one or more cycloalkyl groups having 4 to 8, preferably 5 to 7, carbon atoms, or by 1 or more aromatic groups, such as phenyl or naphthyl groups or substituted phenyl groups. The reaction of the primary alcohol with the phosphorus oxychloride yields the phosphorylation agent of the general formula II.

The reaction of the primary alcohol with phosphorous oxychloride is carried out in the presence of an inert organic solvent, for example halogenated hydrocarbons, such as chloroform or carbon tetrachloride. The reaction is carried out without adding a base. The molar ratio of alcohol to phosphorus oxychloride is generally 1:2, but it may of course be varied within certain limits. For example, 1 mol of alcohol may be reacted with 1.7 to 2.3 mols of phosphorus oxychloride. The reaction is generally carried out under anhydrous conditions. The reaction temperature is generally room temperature but temperatures of −10° to +80° C., for example from 20° C. to 40° C., may also be applied. The reaction time depends on the temperature chosen and ranges from half an hour to 15 hours generally from 10 to 12 hours, when room temperature is applied.

When the reaction which can be controlled by thin-layer chromatography is complete excess phosphorus oxychloride and excess hydrochloric acid may be eliminated in a hydrogen vacuum, for example at 30° to 35° C. The alkyl phosphoric acid dichloride remains as a residue. This alkyl phosphoric acid dichloride may directly be used for the phosphorylation reaction without further purification. A distillation is not necessary. Compared to known phosporylation methods, this is a substantial advantage since many alkyl phosphoric acid dischlorides tend to decompose in an explosive manner.

The phosphorylation agent of the general formula II is very reactive and reacts with a large number of polyhydroxy compounds containing a free hydroxy group. The reaction is preferably carried out with exclusion of moisture in an inert organic solvent, for example a chlorinated hydrocarbon, such as chloroform or carbon tetrachloride. Other organic solvents, such as toluene or xylene or benzene may also be used; absolute solvents are however preferred.

The reaction of the phosphorylation agent with the polyhydroxy compound may be carried out within a wide range of temperature, for example from −10° C. to +50° C., preferably at room temperature. The reaction time used depends on the reaction temperature chosen, it ranges generally from half an hour to 5 or 6 hours. The phosphorylation reaction is preferably carried out in the presence of a base, for example of triethyl amine.

The phosphorylation agent obtained according to this invention allows a number of alkyl esters of phospholipid acid to be obtained. As polyhydroxy compounds, any polyhydroxy compounds may be used which contain a free hydroxy group and the other hydroxy groups of which are protected, for example by esterification, etherification, acetal or ketal formation. In general, the polyhydroxy compound used is a glyceride or a correspondingly higher homolog. It is thus possible according to the invention to phosphorylate erythritol, pentitol or hexitol derivatives but also cyclic polyhydroxy compounds, such for example as cyclic saccharic alcohols. Generally, monosaccaride derivatives and oligo-saccharide derivatives may be used according to the process of the invention.

The process of the present invention may be carried out using racemic mixtures of pure optical isomers. The present invention also provides the products obtained according to the process of this invention. As already mentioned above, this process yields a large variety of different alkyl esters of phospholipid acid, of which individual groups are hereinafter cited as example that can be prepared according to the process of the invention.

1. Alkyl esters of phospholipid acid

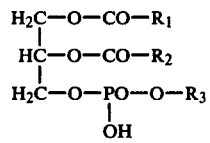

-continued

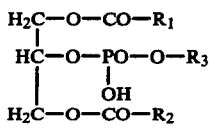

IV

In the formulae III and IV, R₃ is defined as above. $R_1$ and $R_2$ each stand for a saturated or unsaturated straight-chain or branched alkyl group having 5 to 25, 5 to 21 or 5 to 18, 5 to 16 carbon atoms, which may also be substituted by 1 or more, i.e. 2, 3, 4 and more halogen atoms, such as fluorine, chlorine, bromine or iodine atoms. The alkyl groups may also be substituted by a cycloalkyl group or an aromatic ring. If the alkyl groups are substituted by a cycloalkyl group, this may contain 4 to 8, preferably 5, 6 or 7, carbon atoms. If the alkyl groups are substituted by an aromatic ring, this may for example be a phenyl ring or a naphthyl ring which may also carry further substituents.

Starting substances are racemic or optically active 1,2- or 1,3-diglycerides having saturated, unsaturated, branched or halogenated fatty acids or fatty acids which contain a cycloalkane or aromatic ring.

2. Lyso compounds of compounds of Group 1

Starting compounds are 1-acyl-2-benzyl glycerols or 1-benzyl-2-acyl glycerols. The phosphorylation reaction provides the lyso compounds by catalytic debenzylation. Unsaturated compounds are prepared with the help of protective groups which may be eliminated by a mild acid hydrolysis.

The starting compounds may also be obtained by biochemical methods from the compounds of Group 1 by enzymatic splitting with the phospholipases $A_1$ and $A_2$.

3. Analogs with saccharic alcohols

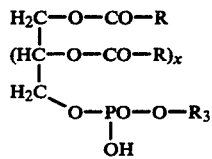

V

In the above formula V, $R_3$ is defined as above, and R has the same meaning as $R_1$ and $R_2$, and X stands for zero or an integer of from 1 to 5, i.e. 0, 1, 2, 3, 4 or 5.

Starting substances are acylated saccharic alcohols which contain a free hydroxy group.

4. Ether analogs of the compounds of Groups 1 to 3 and ether/ester analogs of the groups of compounds 1 and 3, for example

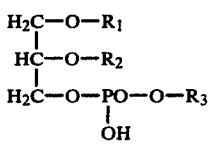

VI

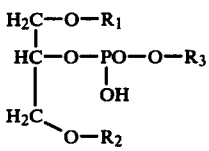

VII

In the formulae VI and VII, $R_1$, $R_2$ and $R_3$ are defined as above.

Starting substances are 1,2- and 1,3-dialkylglycerol ethers or acylglycerol alkyl ethers. The alkyl radicals may be saturated, unsaturated, branched or halogenated and may also contain a cycloalkane or an aromatic ring.

5. Dialkyl ketone glycerol phosphoric acid alkyl esters

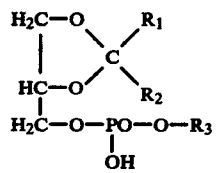

VIII

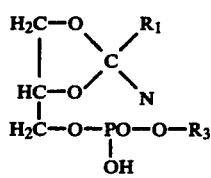

IX

In the above formulae VIII and IX, $R_1$, $R_2$ and $R_3$ are defined as above.

Starting substances are the 1,2- and 1,3-dialkyl ketone glycerols or the corresponding acetals which may be obtained from glycerol or 2-benzyl glycerol by reaction with the corresponding ketones or aldehydes. The ketones or aldehydes may be saturated, unsaturated, branched or halogenated and may also contain a cycloalkane or an aromatic ring.

6. Cycloalkyl ketone glycerol phosphoric acid alkyl esters

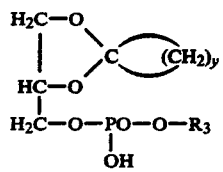

X

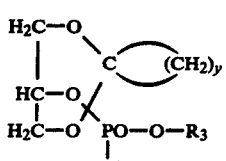

XI

In the above formulae, $R_3$ is defined as above, and y stands for an integer of from 5 to 32, for example 5 to 28, 5 to 24, 5 to 18, 5 to 16, 5 to 14, 5 to 12, 5 to 10, 5 to 8.

Starting substances are 1,2- and 1,3-cycloalkyl ketone glycerols which may be obtained from glycerol or 2-benzylglycerol by reaction with the corresponding cycloalkanone.

7. Alkyl esters of desoxylyso phospholipid acid

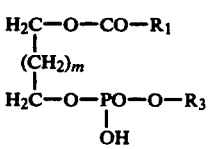

XII

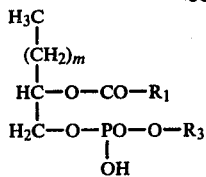

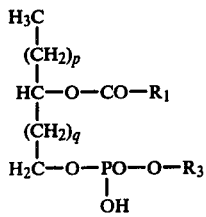

In the above formulae, $R_1$ and $R_3$ are defined as above, and m stands for zero or for an integer of from 1 to 14, for example for 0, 1, 2, 3, 4, 5, 6, 7, 8, 9, 10, 11, 12, 13, and $p+q=m$.

As starting substances, the monoacylalkane diols are preferred. The alkane diols may be saturated, unsaturated, branched or halogenated and may also contain a cycloalkane or an aromatic ring.

8. Ether analogs of compounds of Group 6

Methods for the preparation of the said starting substances are known (s. publication of A. J. Slotboom and P. P. N. Bonsen "Chem. Phys. Lipids" (1970), pages 301 to 398).

The compounds of the invention corresponding to formulae I, III to VI have valuable pharmacological properties and they are potent surfactants which, owing to their structural analogy with the pospholipids present in the cell membranes, are able to influence the surface activity of these membranes. Their negative charge at physiological pH-values is moreover capable of influencing the charge of biological membranes.

Owing to these properties, these substances can be expected to modify the activity of pharmaceuticals by increasing their absorbability and their distribution in the organism. The compounds are valuable additives in the manufacture of drugs.

The compounds of formulae I and III to IV are readily dispersible in water and give emulsions which are stable over a wide pH range. It is surprising that these emulsions are even still stable at a pH of 1.0 whilst, for example, emulsions of lecithin precipitate in flakes already at a pH of 2.0. Dispersions of the said compounds are also suitable to pass unchanged through the stomach (pH 1.5) and to improve, for example, the absorbability of fats.

The compounds of formulae II, VII and VIII are potent surfactants and have a lytic activity on natural membranes (for example erythrocytes). They may therefore be used in many ways for the disintegration of these membranes or, when applied in sublytic dosages, for a modification of the properties of membranes, which again may influence the activity of pharmaceutical compositions.

The compounds of the invention generally have very good emulsifying properties. Having a structure similar to that of natural products, they are physiologically acceptable in foodstuffs and may therefore be used for a variety of applications. When added to margarine, they bring about a better linkage to water, thus preventing it from spattering in the frying pan and imparting to it butter like properties when used for frying. They may be used in sweets for emulsifying syrup with fat and also prevent the fat getting rancid. When applied for cosmetic purposes and for the making of soaps small additions of the products of the invention improve the softness and absorption of ointments, creams, tooth pastes, soaps and the like.

The following examples illustrate the invention.

EXAMPLE 1

General preparation of alkylphosphoric acid dichlorides: 80 g (0.6 mol) of $POCl_3$ (freshly distilled, boiling point 105° to 107° C.) in 100 ml of absolute chloroform (distilled for 90 minutes with circulation over $P_2O_5$) were placed in a three-neck flask equipped with cooler, dropping funnel and nitrogen inlet tube. While stirring by means of a magnetically operated stirrer nitrogen was slowly fed in, and 0.3 mol of the a specified alcohol in 50 ml of absolute chloroform was added dropwise. The mixture was stirred for 12 hours at room temperature, and the resulting hydrogen chloride, excess $POCl_3$ and chloroform were eliminated at 30° C. in the rotary evaporator. To eliminate any trace of $POCl_3$, 50 ml of toluene were added and likewise drained off.

The remaining oily substance, i.e. the alkyl-phosphoric acid dichloride, can be reacted further without purification. Distillation was performed on some of low boiling alkyl phosphoric acid dichlorides and the following boiling points were observed:

|  | boiling point at 10 mm Hg |
|---|---|
| $CH_3$—O—PO—$Cl_2$ | 44° to 47° C. |
| $C_2H_5$—O—PO—$Cl_2$ | 54° to 56° C. |
| $C_3H_7$—O—PO—$Cl_2$ | 66° to 68° C. |
| $C_4H_9$—O—PO—$Cl_2$ | 85° to 87° C. |

The reaction provided a yield of 90 to 100% and can be controlled by thin-layer chromatography.

EXAMPLE 2

Preparation of ω-bromoalkyl-phosphoric acid dichlorides:

(a) Preparation of bromo alcohols having different chain length according to a simple process:

Compounds of formula

in which n stands for the integer of 4 to 10, were synthesized. The starting products were diol of corresponding chain length having terminal alcohol groups. Since only one bromine atom per diol molecule was to be introduced, a method had to be chosen wherein the reaction product was immediately eliminated from the proper reaction medium and thus the possibility of further reaction was excluded. For this purpose the extraction method was suitable.

In a round flask the diol and hydrobromic acid were placed. The starting products were overlaid with petroleum benzine or with benzene/petroleumbenzine. The selection of the extraction agent depended on the insolubility of the diol and on the good solubility of the reaction products therein. The round flask was equipped with a reflux condenser. While energetically stirring by means of a magnetically operated stirrer, the mixture was then refluxed by means of an adequate heating device until the starting product had completely reacted. The progress of the reaction was checked by means of thin-layer chromatograms.

Subsequently the extraction medium phase was separated and dried with calcium sulfate. After the siccative drying agent had been filtered off the extraction medium was eliminated in a rotary evaporator. The residue was subjected to a fractional distillation in an oil pump vacuum.

The yields were about 80 to 95% of the theoretical yield, calculated on the diol used.

4-Bromobutanol-(1) and 5-bromopentanol-(1) were prepared as follows:

0.25 mol=22.5 g of 1,4-butanediol or 26 g of 1,5-pentanediol, 0.48 mol=80 g of HBr(47%), 500 ml of benzene and 50 ml of petroleumbenzine, boiling point 100° to 140° C., were refluxed for 6.5 and 6 hours, respectively.

The rest of the brominated alcohols was prepared as follows:

0.25 mol=29.6 g of 1,6-hexanediol or the corresponding diol, 0.48 mol=80 g of HBr(47%), 1500 ml of petroleum benzine, boiling point 100° to 140° C., were refluxed.

| Reaction product | Reaction time | | physical constants |
|---|---|---|---|
| 4-bromobutanol-(1) | 6,5 | hr | b.p.(0.7mm Hg)58° to 60° C. |
| 5-bromopentanol-(1) | 6 | hr | b.p.(0.5mm Hg)72° to 74° C. |
| 6-bromohexanol-(1) | 1.5 | hr | b.p.(0.6mm Hg)85° to 87° C. |
| 7-bromoheptanol-(1) | 1.5 | hr | b.p.(0.5mm Hg)87° to 89° C. |
| 8-bromooctanol-(1) | 1 | hr | b.p.(0.5mm Hg)110° to 112° C. |
| 9-bromononanol-(1) | 1 | hr | b.p.(0.4mm Hg)112° to 114° C. |
| 10-bromodecanol-(1) | 30 | min | b.p.(0.3mm Hg)124° to 126° C. |

Including 8-bromooctanol-(1) the reaction products were colourless liquids. 9-Bromononanol(1) and 10-bromodecanol-(1) are white and solid products at room temperature. Brominated alcohols of greater chain length may principally be prepared according to the same process. Since these reaction products are all solid products, they are purified by recrystallization.

(b) Preparation of ω-bromoalkylphosphoric acid dichloride: 32 mmol=30 ml of phosphorus oxytrichloride (freshly distilled, boiling point 105° to 107° C.) in 70 ml of absolute chloroform (distilled for 90 minutes with circulation over $P_2O_5$) were placed in a round flask. At room temperature, nitrogen was introduced into the solution for a short time to expel air. The flask was equipped with a dropping funnel and sealed air-tight. While stirring by means of a magnetically operated stirrer, 20 mmol of the brominated alcohol of desired chain length in 50 ml of absolute chloroform were added dropwise slowly at room temperature with the exclusion of moisture. Stirring was continued for about 12 hours. The hydrogen chloride resulting from the reaction as well as excess phosphorus oxytrichloride and chloroform were eliminated at 30° C. in the rotary evaporator. To eliminate every trace of phosphorus oxytrichloride toluene was added and likewise drained off.

The yield was 95 to 100% and the conversion reaction can be checked by thin-layer chromatography.

EXAMPLE 3

General preparation of alkylesters of phospholipid acid and of structural analogues thereof:

The phosporylation agent prepared in Example 1 or 2 (0.3 mol) was dissolved in 100 ml of absolute chloroform (distilled for 90 minutes with circulation over $P_2O_5$), and the solution was cooled to 0° to 5° C. in an ice bath. While stirring by means of a magnetically operated stirrer, 60 g (0.6 mol) of absolute triethylamine (dried over lithiumaluminumhydride and freshly distilled) were added dropwise to 50 ml of absolute chloroform. The ice bath was then replaced by a water bath of 20° C. While steadily stirring, a solution of the corresponding starting substance (0.15 mol) in 150 ml of absolute chloroform was added dropwise to the phosporylation mixture. Checking by means of thin-layer chromatography made sure that the reaction was almost complete already after the dropwise addition. After another 6 hours at 40° C. the reaction mixture was freed in the rotary evaporator at 35° C. from solvent, and the residue was taken up in 450 ml of tetrahydrofuran. While stirring, 1 M sodium acetate solution of pH 8.4 was added to the suspension or solution of the reaction mixture in tetrahydrofuran until the water phase remained neutral (pH about 7). For this purpose, about 450 ml of 1 M sodium acetate solution had to be added. The hydrolysed reaction product was extracted as the sodium salt by means of 450 ml of diisopropylether. The water phase was again extracted by means of 200 ml of diisopropylether. The combined diisopropylether extracts were mixed while stirring with 10 g of sodium carbonate to eliminate water and to assure a complete conversion of the reaction product into the sodium salt.

For the preparation of derivatives having less than a total of 14 carbon atoms, the reaction solution was acidified with HCl (pH about 2) prior to the extraction with diisopropyl ether. Derivatives having a very short chain were better extracted as the free acids and can be crystallized by carefully adding sodium methylate in methanol.

The diisopropylether phase was filtered and the filtrate was evaporated in vacuo. The residue was recrystallized from ethylmethylketone acetone mixtures. Generally the resulting reaction products are analytically pure. Otherwise a complete purification of the products is brought about by chromatography on silica gel. The yields of analytically pure product vary between 70 and 90% (calculated on the starting products used).

The following compounds were prepared:

Compound of Group 1:

sn-1,2-dimyristoylglycerol-3-phosphoric acid methyl ester, as sodium salt, $C_{32}H_{62}NaO_8P$ (628.8)

Calculated: C 61.12% H 9.94% P 4.93%.

The data found agreed with the calculated values.

Compound of Group 2:

sn-1-myristoylglycerol-3-phosphoric acid methyl ester, as sodium salt, $C_{16}H_{36}NaO_7P$ (418.5)

Calculated: C 51.67% H 8.67% P 7.40%.

The data found agreed with the calculated values.

Compound of Group 3:

1,2,3,4,5-pentapalmitoyl-D-mannitol-6-phosphoric acid butyl ether, as sodium salt, $C_{90}H_{172}NaO_{14}P$ (1532.3)

Calculated: C 70.55% H 11.32% P 2.02%.

The data found agreed with the calculated values.

Compound of Group 4:

Glyceroldioctyl ether phosphoric acid-(3)-β-bromoethyl ester, as sodium salt, $C_{21}H_{43}BrNaO_6P$ (525.5)

Calculated: C 48.00% H 8.25% Br 15.21% P 5.90%.
The data found agreed with the calculated values.
Compound of Group 5:
Diheptadecyl ketone glycerol-3-phosphoric acid octyl ester, as sodium salt, $C_{46}H_{92}NaO_6P$ (795.21)
Calculated: C 69.48% H 11.66% P 3.90%.
The data found agreed with the calculated values.
Compound of Group 6:
Cyclopentadecyle ketone glycerol-3-phosphoric acid-$\beta$-bromoethylester, as sodium salt, $C_{20}H_{37}BrNaP$ (484.4)
Calculated: C 49.59% H 7.70% Br 16.49% P 6.39%.
The data found agreed with the calculated values.
Compound of Group 7:
Oleoylhexanediol-(1,6)-phosphoric acid isopropyl ester, as sodium salt, $C_{27}H_{52}NaO_6P$ (526.68)
Calculated: C 61.57% H 9.52% P 5.88%.
The data found agreed with the calculated values.
Compound of Group 8:
Propanediol-(1,3)-hexadecyl ether phosphoric acid hexyl ester, as sodium salt, $C_{25}H_{52}NaO_5P$ (486.7)
Calculated: C 61.70% H 10.77% P 6.37%.
The data found agreed with the calculated values.

We claim:

1. An alkyl ester of a phospholipid acid of the formula

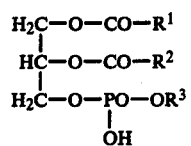

wherein $R^1$ and $R^2$ are the same or different and each stands for a substituted or unsubstituted alkyl of 5 to 25 carbon atoms or haloalkyl of 6 to 25 carbon atoms and $R^3$ is alkyl of 6 to 18 carbon atoms.

2. An alkyl ester of a phospholipid acid of the formula

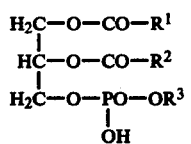

wherein $R^1$ and $R^2$ are selected from substituted and unsubstituted linear and branched alkyl of 5 to 25 carbon atoms and $R^3$ is selected from saturated and unsaturated, straight chain and branched alkyl of 6 to 18 carbon atoms which may be substituted by halogen, and the physiologically acceptable salts thereof.

3. The compound sn-1,2-dimyristoyl glycerol-3-phosphoric acid hexyl ester.

* * * * *

UNITED STATES PATENT AND TRADEMARK OFFICE
CERTIFICATE OF CORRECTION

PATENT NO. : 4,160,773
DATED : July 10, 1979
INVENTOR(S) : Eibl et al.

It is certified that error appears in the above-identified patent and that said Letters Patent are hereby corrected as shown below:

In the Heading, Item [63] and in column 1, line 8, the date "Aug 5, 1976" should be --Aug 5, 1975--.

Signed and Sealed this

Ninth Day of October 1979

[SEAL]

Attest:

RUTH C. MASON
*Attesting Officer*

LUTRELLE F. PARKER
*Acting Commissioner of Patents and Trademarks*